United States Patent [19]

Densow

[11] Patent Number: 4,610,657
[45] Date of Patent: Sep. 9, 1986

[54] URETERAL STENT

[75] Inventor: David C. Densow, Racine, Wis.

[73] Assignee: Medical Engineering Corporation, Racine, Wis.

[21] Appl. No.: 771,161

[22] Filed: Aug. 30, 1985

Related U.S. Application Data

[63] Continuation of Ser. No. 567,757, Jan. 3, 1984, abandoned.

[51] Int. Cl.⁴ ............................................ A61M 25/00
[52] U.S. Cl. .......................................................... 604/8
[58] Field of Search ........................................ 604/8–10, 604/95, 164, 170, 280–282

[56] References Cited

U.S. PATENT DOCUMENTS

| | | | |
|---|---|---|---|
| 1,920,006 | 7/1933 | Dozier | 604/170 |
| 4,212,304 | 7/1980 | Finney | 604/8 |
| 4,307,723 | 12/1981 | Finney | 604/8 |

FOREIGN PATENT DOCUMENTS 193855  1/1965  Sweden ............................. 604/170

OTHER PUBLICATIONS

"A New Arteriovenous Shunt Design", Ersek, Robert A. et al., Trans. Amer. Soc. Artif. Int. Organs,—vol. XV—1969.
Jol. Urology, vol. 119, Jun. 1978, "Self-Retained Internal Ureteral Stents: A New Approach", Hepperlen et al., pp. 731–734.

Primary Examiner—P. E. Konopka
Attorney, Agent, or Firm—Quarles & Brady

[57] ABSTRACT

An ureteral stent comprises an elongated, flexible tubular member which has proximal and distal ends in the form of hooks. Both of the ends of the member are open but the opening at the proximal end is smaller than the lumen or the opening at the distal end. Methods of inserting the stent, maneuvering the stent past difficult obstructions in the ureter, replacing an indwelling stent are described, as well as kits for performing those methods.

3 Claims, 9 Drawing Figures

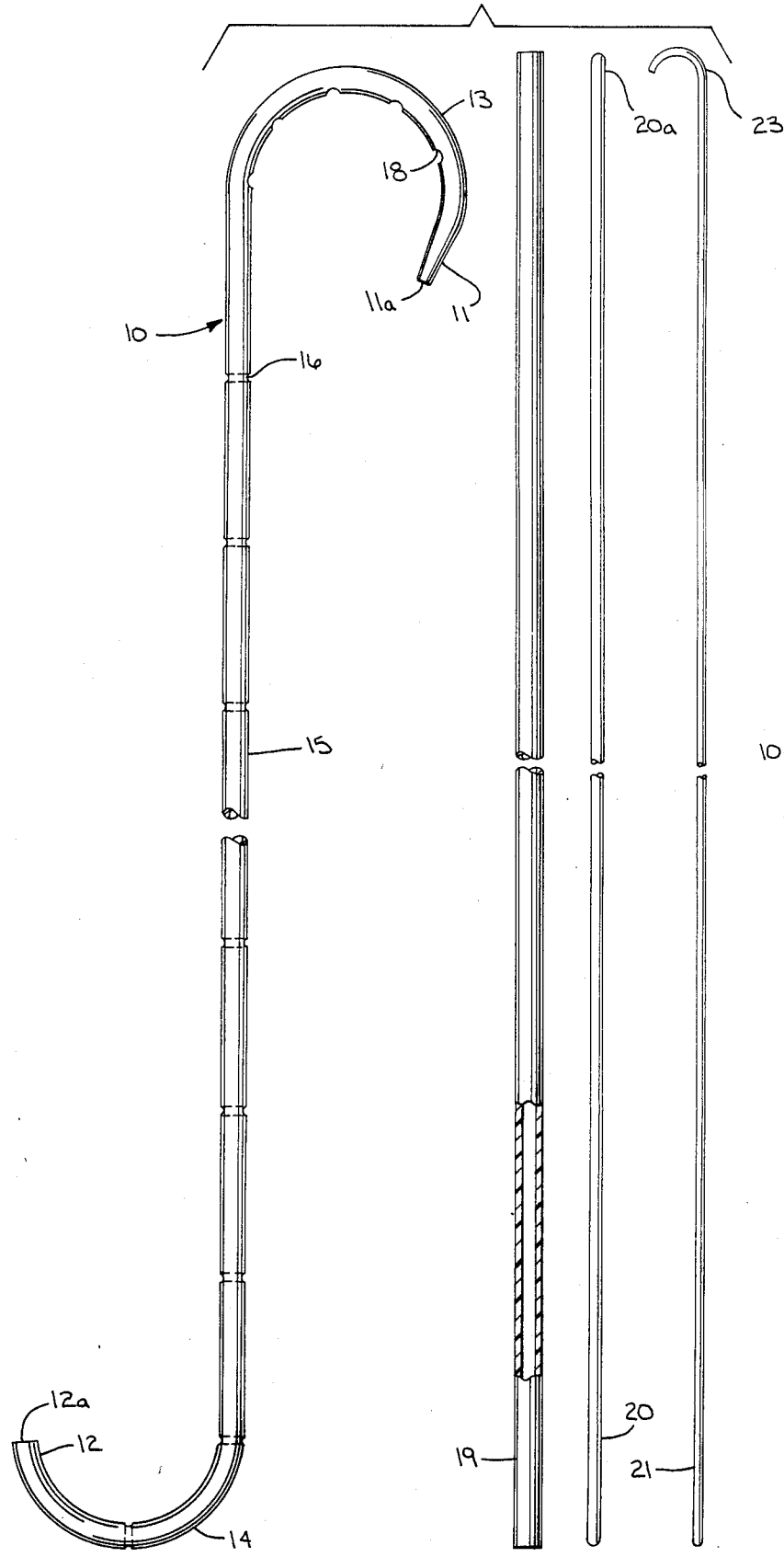
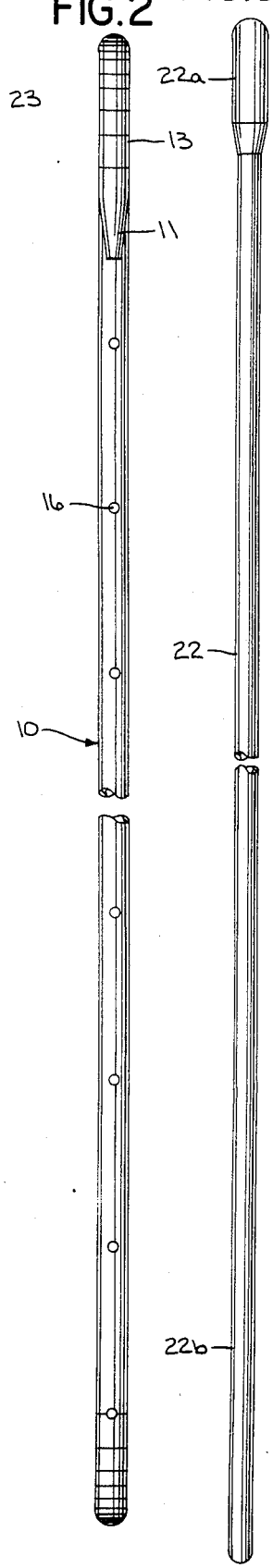

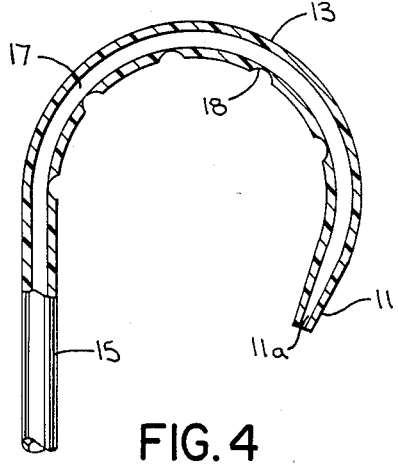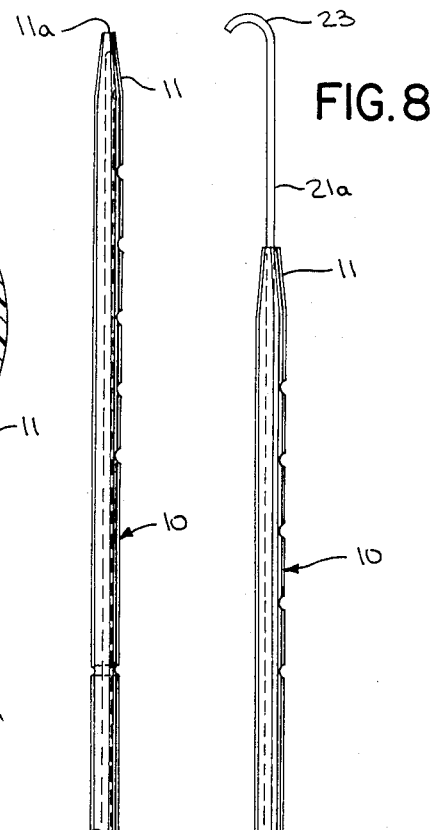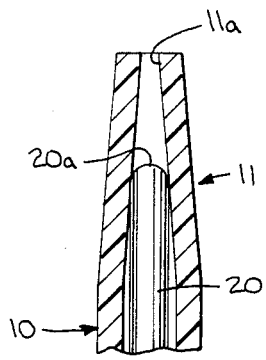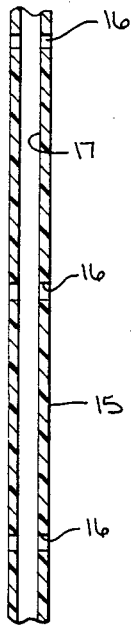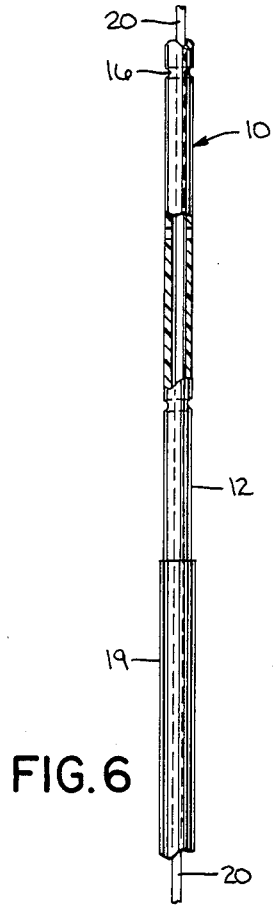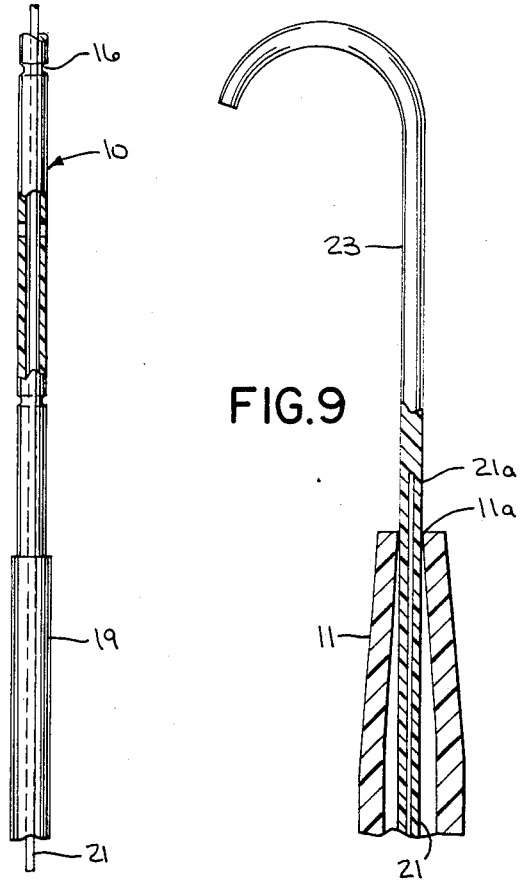

URETERAL STENT

This application is a continuation of application Ser. No. 567,757, filed Jan. 3, 1984, now abandoned.

FIELD OF THE INVENTION

The present invention relates to ureteral stents. More particularly, it relates to a novel stent which can be used to bypass obstructions and which is more easily replaced than existing stents.

BACKGROUND OF THE INVENTION

Indwelling ureteral catheter stents or drainage tubes have been used to bypass ureteral obstructions or uretero-vaginal fistulas and maintain urinary drainage. In the past, stents made of straight lengths of open end tubing have been used for this purpose and have provided good drainage for sustained periods of time. However, the use of such open end tubing has not been completely satisfactory. For example, in some instances, the tubing has migrated and in others it has been expelled.

Various attempts have been made to produce stents which do not have the problems which accompany the use of such tubing. For example, stents have been designed which are closed at one end to facilitate passage into a body passage and which have at the other end a flange to make upward migration of the stent less likely. Another approach has been to provide the body of the stent with sharply pointed barbs which are designed to prevent downward migration and expulsion. However, such barbs increase the diameter of the stent making it more difficult to insert and in some instances can cause the stent to migrate outside the bladder.

In U.S. Pat. No. 4,212,304 issued July 15, 1979 and U.S. Pat. No. 4,307,723 issued Dec. 29, 1981, ureteral stents are disclosed which have hooks at each end which are surprisingly effective in preventing migration and expulsion. The patented stents are widely accepted because they can be easily introduced both endoscopically and during open surgery.

All the commercially available stents have several disadvantages in common. If they are soft and flexible enough to not cause patient discomfort it is difficult to maneuver them past obstructions in the ureter and if they must be removed they are difficult to replace.

SUMMARY OF THE INVENTION

It is an object of the present invention to disclose a novel ureteral stent which is soft and flexible enough for patient comfort and which can be used to bypass obstructions of the ureter.

It is another object to disclose a method of bypassing an obstruction in the ureter using the stent and a kit for practicing the method.

It is a further object to disclose a method of replacing the stent of the present invention and a kit for practicing the method.

The ureteral catheter stent of the present invention comprises an elongated, flexible tubular member of substantially uniform outside surface throughout its length having proximal and distal ends which are open. The proximal end of the tubular member is set in the form of a hook and has an opening which is relatively smaller than that in the distal end.

The stent is preferably made of a soft, flexible, radiopaque material and may be provided with indicating means which can be seen through a cystoscope and which will show the direction the proximal hook will extend when the stent is in place.

The stent is generally put in place by inserting a guide wire through the distal opening and into the lumen. The guide wire used for this purpose has a leading end which is larger than the proximal end opening. The guide wire is inserted until the leading end reaches the proximal opening. Because the guide wire is relatively stiff the hook is straightened in the process. Next, a stent pusher is threaded over the free end of the guide wire behind the stent to aid the passage of the stent through a cystoscope.

In the event that an obstruction in the ureter is encountered which prevents positioning the stent in the normal manner, the stent and guide wire are removed and the stent is threaded upon a second smaller diameter guide wire with a tip that will pass through the opening in the proximal end. The smaller guide wire is introduced into the ureter and using standard retrograde catheterization and a cystoscope the leading end and the tip of the guide wire is manuevered past the obstruction. When the tip and leading end of the smaller guide wire have reached the desired position in the lower calix or renal pelvis, the stent is advanced over the guide wire and properly positioned using a stent pusher. The guide wire is then withdrawn and the stent pusher disengaged, if necessary, from the stent.

When for some reason it is desired to replace the stent, the open distal end of the stent is located and the smaller diameter guide wire is inserted through the stent to straighten the hook. The stent is then completely removed leaving the smaller guide wire in place. A second replacement stent is then run over the smaller guide wire and advanced into position using a stent pusher. When the replacement stent is properly positioned, the stent pusher and the smaller diameter guide wire are withdrawn.

The above stated and other objects and advantages of the invention will be apparent from the description which follows:

DESCRIPTION OF THE DRAWINGS

FIG. 1 is an elevational view of the preferred embodiment of the stent, the stent pusher and the guide wires of the present invention;

FIG. 2 is a view of the back of the stent of FIG. 1;

FIG. 3 is an elevational view of a guide wire with an an enlarged proximal end.

FIG. 4 is a enlarged view partly in section of the proximal end of the stent of FIG. 1;

FIG. 5 is an enlarged sectional view of a body portion of the stent of FIG. 1;

FIG. 6 is an elevational view showing the larger guide wire in the stent and the hooks straightened;

FIG. 7 is an enlarged sectional view of the proximal end of the stent and the guide wire of FIG. 6;

FIG. 8 is an elevational view similar to FIG. 6 but showing the smaller guide wire in the stent; and FIG. 9 is an enlarged sectional view of the proximal end of the stent and smaller guide wire of FIG. 8.

DESCRIPTION OF PREFERRED EMBODIMENT

In the preferred embodiment shown in FIG. 1, the stent 10 is seen to be an elongated tubular member having a proximal end 11 and a distal end 12. Portions adjacent each of the ends 11 and 12 are formed and set in the shape of gently curved hooks 13 and 14 which extend in opposite directions.

The two gently formed opposed hooks 13, 14 of the stent prevent it from migrating either upwardly or downwardly once it is in place. A suitable material may be incorporated into the hooks 13 and 14 to make them less flexible and therefore make the stent more resistant to migration. The hooks 13 and 14 extend in opposite directions so that when the stent 10 is used as an indwelling ureteral stent the proximal end 11 can hook into the lower calix or renal pelvis while the distal end 12 curves out into the bladder. This design also prevents the tip of the stent from impinging directly into the bladder mucosa thereby decreasing discomfort and inflammation.

The stent 10 includes a relatively straight intermediate section 15 which extends between the proximal hook 13 and the distal hook 14.

The stent 10 is made of a suitable flexible material such as nylon which is soft and stiff enough for the intended purpose and which preferably contains a radiopaque material. The stent may be supplied in 7 French and 8.5 French sizes in 16, 24, 26, 28 and 30 cm lengths. The listed length of the stent 10 is the length of the section 15 and does not include the hooked ends 13 and 14. This allows the user to radiographically estimate the ureteral length and select the proper stent for passage.

Referring now to FIGS. 1, 2, 4 and 5, it can be seen that the stent 10 has radial drainage passage 16 which connect the lumen 17 of the stent 10 to the outside and permit inside/outside drainage. The drainage passages 16 are located about 5 centimeters apart on both sides of the straight section 15. As best seen in FIG. 5, the passages 16 of both sides are preferably aligned. Returning to FIGS. 1 and 4, it can be seen that there are similar but larger openings 18 in the inside wall of the proximal hook 13.

Referring again to FIG. 1, there also can be seen a stent pusher 19, a relatively large diameter guide wire 20 which is normally used to position the stent 10 in a body passage, and a smaller diameter guide wire 21 which is used to bypass difficult obstructions and to replace the stent. In FIG. 3, a guide wire 22 is shown which has an enlarged proximal end 22a; it also can be used in the normal placement of the stent 10 and to bypass obstructions.

The stent 10 is supplied with both ends 11 and 12 open. As best seen in FIG. 4, the proximal end opening 11a is smaller than the distal end opening 12a or the lumen 17. When normal endoscopic insertion is employed, the relatively large diameter guide wire 20 is introduced into the lumen 17 of the stent 10 to straighten both hooks 13 and 14 as seen in FIG. 6. When this is done the end 20a of the guide wire 20 is prevented from leaving the lumen 17 of the stent 10, as seen in FIG. 7, because of the relatively small proximal opening 11a.

To assist in properly positioning the stent 10, the stent pusher 19 is threaded over the free end of the guide wire 20. If the stent pusher 19 is small enough it can be force fit into the distal opening 12a; this allows for the partial withdrawal and redirection of the stent, if necessary, during standard retrograde catheterization. The stent pusher 19 is then used to advance the stent 10 into position. Once the stent 10 is properly positioned, the guide wire 20 and the stent pusher 19 are removed by withdrawing the stent pusher 19 while holding the guide wire 20 thus causing the stent 10 and stent pusher 19 to separate after which the guide wire 20 and then the stent pusher 19 are withdrawn.

When an obstruction in the ureter is encountered that cannot be bypassed by the stent 10 using the normal method of introduction, the stent 10 and guide wire 20 are withdrawn and the stent 10 is threaded on the smaller diameter guide wire 21 which has a forgiving, unreinforced tip 23 on its proximal end 21a (seen best in FIGS. 8 and 9). The forgiving, unreinforced tip 23 minimizes the possibility of damage being caused to the body by the guide wire 21. The tip 23 and proximal end 21a of the guide wire 21 are passed through the proximal opening 11a of the stent and maneuvered past the obstruction in the ureter. When it is known that the tip 23 and the proximal end 21a are safely past the obstruction, the stent 10 is advanced over the guide wire 21 past the obstruction and pushed into place with the stent pusher 19. The guide wire 21 is then withdrawn and the stent pusher 19 is disengaged from the stent 10.

The guide wire 22 can be used in a similar manner to position the stent 10 and to bypass an obstruction. When no difficulty with obstructions is anticipated, the enlarged head 22a of the guide wire 22 is introduced first into the lumen 17 of the stent 10. When difficult obstructions are encountered the opposite end 22b of the guide wire 22 is introduced first into the lumen 17 and the stent is maneuvered past the obstruction in the same manner as described with stent 21.

When it is desired to replace an indwelling stent of the present invention, the radiopaque stent is first cystoscopically visualized and then a foreign body forceps or a retractable type stone basket (neither shown) is used to retract the stent 10 until the distal end 12 can be reached; care, of course, must be taken to not retract the stent 10 past any obstructions in the ureter. Next, the proximal end 21a and tip 23 of the smaller guide wire 21 are threaded through the distal opening 12a into lumen 17 of the stent 10 and advanced to straighten the hooks 13 and 14 (as seen in FIG. 8). The guide wire 21 is further advanced until the proximal end 21a and tip 23 pass through the proximal opening 11a as seen in FIGS. 8 and 9. The stent 10 is then withdrawn without removing the guide wire 21. A new stent is threaded proximal end first over the guide wire 21 and advanced as previously described into the proper position, e.g. into the bladder, through the ureter and into the kidney. When the new stent is properly in place, the guide wire 21 is then withdrawn.

The ureteral catheter stent 10 of the present invention is preferably made of nylon which has a durometer between about 70 Shore 'A' and about 55 Shore 'D' to which 10% barium sulfate has been added as the radiopaque agent. Stents made of this material have been found to be soft enough not to cause undue discomfort to the patient and stiff enough to bypass obstructions in the ureter. Other plastic materials such as silicone rubber which possess the desired properties and resist encrustation with urine salts can also be used.

The stent 10 is preferably formed by extruding a length of tubing of the desired size and durometer. The proximal end 11 of the tubing is then placed in a mold to reduce the size of the opening 11a to less than the diameter of the larger guide wire 20 and the lumen 17. The length of tubing is then placed in a form to shape the hooks 13 and 14. The drainage openings 16 and 18 may be formed at any step of the process by piercing the wall of the tubing with a flattened, sharpened hole cutter of the desired size or by use of a laser or any other conventional means.

The ureteral catheter stent 10 of the present invention may be supplied as a component of a kit for normal insertion and to bypass difficult obstructions or a kit for replacing an indwelling stent.

A kit for normal insertion and to bypass difficult ureteral obstructions might contain a stent 10 of the desired size and either the two guide wires 20 and 21 or the combination guide wire 22 (seen only in FIG. 3).

A kit for replacing an indwelling stent would include a replacement stent 10 and a guide wire 21.

A stent pusher 19 may be supplied as a component of either of the kits or a satisfactory stent pusher 19 also may be made from a half length of a relatively stiff standard ureteral catheter, preferably 5 French.

In the preferred embodiment described and shown in the drawing, the proximal and distal end portions of the catheter stent are both in the form of gently curved hooks. However, it is to be understood that the term "hook" is intended to include other functionally equivalent shapes which prevent migration and do not increase the effective outer diameter of the stent, or complicate its method of introduction.

It will be readily apparent to those skilled in the art that a number of modifications and changes can be made without departing from the spirit of the invention. Therefore, it is to be understood that the scope of the invention is not to be limited by the foregoing description, but only by the claims.

I claim:

1. In a ureteral stent comprising an elongated tubular member of substantially uniform outside diameter throughout its length and having its proximal and distal ends set in the form of hooks, said member having central lumen and at least one drainage opening extending through a wall connecting the lumen to the outside, the improvement which comprises said member having a lumen which tapers inwardly adjacent the proximal end to terminate in an opening at the proximal end which is smaller in diameter than the main portion of lumen, said opening serving to allow the passage of a thin guide wire to maneuver past an obstacle and also serving to block the exit of a thick insertion wire from the lumen so that the thick insertion wire can be used to push the stent into a desired position in a patient's ureter.

2. A kit for use in inserting a stent into an ureter, said kit containing a ureteral stent of claim 1 and a guide wire, said guide wire having one relatively thick end which is smaller than the lumen of the stent and larger than the opening in the proximal end, and an other end which is relatively thinner than both the lumen and the proximal opening, said guide wire serving as both an insertion device by inserting the think end first into the lumen to insert the stent into an unobstructed ureter and as an obstruction bypassing device to bypass an obstruction in the ureter by inserting the other end into the lumen first and out the proximal end of the stent past said obstruction so that the stent can be advanced over the guide wire past the obstruction.

3. A kit for exchanging a new ureteral stent for an indwelling stent in the ureter of a patient, said kit comprising a new ureteral stent of claim 1 and an elongated thin guide wire which is thinner than both the lumen of the stent and the opening in the proximal end so that one end of the guide wire can be inserted into the distal opening and completely through the lumen of the stent and out the proximal opening into the open distal end of an open-ended indwelling stent in the ureter of a patient so that the indwelling stent can be removed by running it out along said guide wire without removing the guide wire and a new ureteral stent can be run up the guide wire into position in the ureter of the patient.

* * * * *